(12) United States Patent
Hirata (10) Patent No.: US 12,178,544 B2
(45) Date of Patent: Dec. 31, 2024

(54) INFORMATION MANAGEMENT SYSTEM, AND PAIRING METHOD FOR MEASUREMENT DEVICE AND INFORMATION TERMINAL

(71) Applicant: OMRON HEALTHCARE Co., Ltd., Kyoto (JP)

(72) Inventor: Hideie Hirata, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 740 days.

(21) Appl. No.: 17/303,996

(22) Filed: Jun. 11, 2021

(65) Prior Publication Data

US 2021/0298602 A1   Sep. 30, 2021

Related U.S. Application Data

(63) Continuation of application No. PCT/JP2019/045080, filed on Nov. 18, 2019.

(30) Foreign Application Priority Data

Dec. 18, 2018 (JP) ................................ 2018-236323

(51) Int. Cl.
*A61B 5/00* (2006.01)
*H04W 12/50* (2021.01)

(52) U.S. Cl.
CPC .......... *A61B 5/0022* (2013.01); *A61B 5/6898* (2013.01); *A61B 5/742* (2013.01); *H04W 12/50* (2021.01)

(58) Field of Classification Search
CPC ....... A61B 5/742; A61B 5/7415; A61B 5/024; A61B 5/021; A61B 5/112; A61B 5/01;
(Continued)

(56) References Cited

U.S. PATENT DOCUMENTS

| 8,738,925 | B1 * | 5/2014 | Park | H04B 7/26 713/186 |
|---|---|---|---|---|
| 2002/0073234 | A1 * | 6/2002 | Ma | H04L 69/04 709/230 |

(Continued)

FOREIGN PATENT DOCUMENTS

| CN | 102484592 A | 5/2012 |
|---|---|---|
| CN | 103997359 A | 8/2014 |

(Continued)

OTHER PUBLICATIONS

International Search Report for International Application No. PCT/JP2019/045080 dated Dec. 17, 2019 (Dec. 17, 2019).

(Continued)

*Primary Examiner* — Daniel L Murphy
*Assistant Examiner* — Amie M Ndure
(74) *Attorney, Agent, or Firm* — Birch, Stewart, Kolasch & Birch, LLP (57) ABSTRACT

An information management system according to the present invention includes one or more measuring devices and one or more information terminals configured to receive information related to measurement values from the one or more measuring devices. When each information terminal receives an input indicating that a measurement value displayed on one of the measuring devices and a measurement value displayed on the information terminal match each other, the information management system pairs the measuring device and the information terminal.

9 Claims, 6 Drawing Sheets

(58) Field of Classification Search
CPC ... A61B 5/6898; A61B 5/0022; H04W 12/50; G16H 40/63; H04M 1/72412
See application file for complete search history.

(56) References Cited

U.S. PATENT DOCUMENTS

| | | | | |
|---|---|---|---|---|
| 2002/0184307 | A1* | 12/2002 | Pineau | H04L 67/563 709/217 |
| 2002/0184318 | A1* | 12/2002 | Pineau | G06F 16/9577 709/206 |
| 2005/0010694 | A1* | 1/2005 | Ma | H04N 1/00106 709/250 |
| 2005/0037779 | A1* | 2/2005 | Ma | H04N 1/00312 455/456.6 |
| 2006/0031126 | A1* | 2/2006 | Ma | H04N 1/00312 705/26.1 |
| 2011/0053558 | A1 | 3/2011 | Teague | |
| 2014/0235166 | A1* | 8/2014 | Molettiere | A61B 5/7405 455/41.2 |
| 2014/0235168 | A1* | 8/2014 | Molettiere | H04W 4/80 455/41.2 |
| 2014/0235171 | A1* | 8/2014 | Molettiere | A61B 5/486 455/41.2 |
| 2014/0281547 | A1 | 9/2014 | Modzelewski et al. | |
| 2015/0172931 | A1* | 6/2015 | Jose | H04W 16/14 370/329 |
| 2015/0257189 | A1* | 9/2015 | Molettiere | A61B 5/02055 455/41.2 |
| 2016/0227484 | A1* | 8/2016 | Park | G08C 17/02 |
| 2017/0311365 | A1* | 10/2017 | Molettiere | H04W 12/33 |
| 2019/0130845 | A1* | 5/2019 | Han | G09G 3/3266 |

FOREIGN PATENT DOCUMENTS

| | | | | |
|---|---|---|---|---|
| CN | 105122706 | A | 12/2015 | |
| JP | 2015-083083 | A | 4/2015 | |
| JP | 2016-512965 | A | 5/2016 | |
| JP | 2017-123144 | A | 7/2017 | |
| TW | 201526866 | A | 7/2015 | |
| WO | 2015/060054 | A1 | 4/2015 | |
| WO | WO-2018049893 | A1 * | 3/2018 | H04L 51/30 |

OTHER PUBLICATIONS

Chinese Office Action and Search Report for Chinese Application No. 201980075148.2, dated Apr. 10, 2024, with an English translation.

* cited by examiner

INFORMATION MANAGEMENT SYSTEM, AND PAIRING METHOD FOR MEASUREMENT DEVICE AND INFORMATION TERMINAL

CROSS-REFERENCE TO RELATED APPLICATIONS

This application is the U.S. national stage application filed pursuant to 35 U.S.C. 365(c) and 120 as a continuation of International Patent Application No. PCT/JP2019/045080, filed Nov. 18, 2019, which application claims priority from Japanese Patent Application No. 2018-236323, filed Dec. 18, 2018, which applications are incorporated herein by reference in their entireties.

TECHNICAL FIELD

The present invention relates to an information management system including a measuring device and an information terminal, and a pairing method of the measuring device and the information terminal.

BACKGROUND ART

In recent years, it has become widespread to perform health management by measuring personal health-related information (also referred to as "health information" hereinafter), such as weight, blood pressure value, and activity level, by a measuring device and recording and analyzing the measurement results by an information terminal, such as a smart phone.

When such health management is performed, preferably the measuring device and the information terminal are connected to each other and the result of measurement by the measuring device can be automatically acquired by the information terminal without a user having to input the result to the information terminal each time. Specifically, for example, a method can be considered in which an information terminal receives measurement information from a measuring device by near-field wireless communication, but under circumstances in which a plurality of measuring devices of the same type are used, it is necessary to prevent erroneous reception of information from measuring devices other than the device that has actually performed the measurement.

In order to solve such problems, it is sufficient to pair a predetermined measuring device and a predetermined information terminal (register a device) and acquire only information from the device with which pairing is established. Pairing is performed by, for example, registering identification characters identifying an individual measuring device in an information terminal, and conventionally a method of manually inputting identification information printed on a case of a device, a seal adhering to the same, or the like into an information terminal has been adopted.

With such a method, the task is complex for the user and may result in erroneous input. In contrast, Patent Document 1 proposes performing pairing by acquiring serial information stated on a measuring device by taking a photo or scanning a bar code of the information using a receiving device.

CITATION LIST

Patent Literature

Patent Document 1: JP 2016-512965 T

SUMMARY OF INVENTION

Technical Problem

Nevertheless, even in the technology set forth in Patent Document 1 described above, the user must capture an image (or scan) the identification information and thus, in this regard, a complex task arises similarly to the related art. Further, the identification information optically discernible needs to be provided on the measuring device, and optical means for capturing an image needs to be provided on the receiving device, resulting in the problem of requiring a cost accordingly.

In light of the related art such as described above, an object of the present invention is to provide a technology that reduces a work burden of a user when pairing a measuring device and an information terminal.

Solution to Problem

To solve the problems described above, an information management system according to the present invention includes one or more measuring devices, and one or more information terminals. Each of the one or more measuring devices includes a sensor configured to measure a predetermined physical quantity, a first display unit configured to display a measured quantity that is a value of the physical quantity measured by the sensor and/or a predetermined value calculated from the physical quantity measured by the sensor, and a first communication unit configured to transmit measurement information including identification information identifying the measuring device, and the measured quantity. Each of the one or more information terminals includes a second communication unit configured to receive the measurement information, a second display unit configured to display a value of the measured quantity included in the measurement information of one of the measuring devices, the measurement information being received by the second communication unit, an input unit configured to receive an input indicating whether or not a value of the measured quantity displayed on the first display unit and the value of the measured quantity displayed on the second display unit match each other, a storage unit configured to store the identification information included in the measurement information received by the second communication unit, and a control unit configured to control the second communication unit, the second display unit, the input unit, and the storage unit. When there is an input, via the input unit, indicating that the value of the measured quantity displayed on the first display unit and the value of the measured quantity displayed on the second display unit match each other, or there is not an input indicating that the value of the measured quantity displayed on the first display unit and the value of the measured quantity displayed on the second display unit do not match each other within a predetermined time, the control unit stores, in the storage unit, the identification information of the measuring device that has transmitted the measurement information including the value of the measured quantity.

Here, the measuring device described above includes various measuring devices such as body information measuring devices, activity measuring devices, and environmental information measuring devices. Examples of the body information measuring devices include a scale, a body composition meter, a blood pressure monitor, a heart rate monitor, and a thermometer. Examples of the activity measuring devices include a pedometer and an activity meter provided in various fitness devices. Examples of the environmental information measuring devices include a temperature and humidity meter, a noise meter, and an illuminometer. Further, depending on the measuring device, the measured quantity includes values of various quantities such as body information, activity levels, and environmental information. Examples of the body information include weight, body fat percentage, blood pressure, heart rate (pulse), and body temperature. Examples of the activity levels include the number of steps, travel distance, and calorie consumption. Examples of the environmental information include room temperature, humidity, noise level, and illuminance.

Further, the information terminal described above includes mobile information terminals such as a smart phone, a tablet terminal, and a laptop computer as well as a stationary information terminals. Further, the "first communication unit" described above may be a transmission means that performs transmission only, or may be a transmission and reception means capable of reception as well. Further, the "second communication unit" described above may be a reception means that performs reception only, or may be a transmission and reception means capable of transmission as well.

According to the configuration of a system such as described above, a task performed by a user to pair a measuring device and an information terminal is simple confirmation that a value displayed on a display unit of a measuring device and a value displayed on a display unit of an information terminal match each other, and thus the user burden for pairing can be markedly reduced.

Further, in the information management system described above, in a case in which the second communication unit receives the measurement information transmitted from a plurality of the measuring devices, when there is not an input indicating that the value of the measured quantity displayed on the first display unit and the value of the measured quantity displayed on the second display unit match each other within a predetermined time, or there is an input, via the input unit, indicating that the value of the measured quantity displayed on the first display unit and the value of the measured quantity displayed on the second display unit do not match each other, the control unit displays, on the second display unit, a value of the measured quantity included in the measurement information related to another of the plurality of the measuring devices, the measurement information being received by the second communication unit.

Further, the measuring device may be any one of a scale, a body composition meter, a blood pressure monitor, a pulse meter, a thermometer, or a pedometer. Further, the information terminal may be a smart phone.

Further, a communication unit of the measuring device may be a speaker, and a receiving unit of the information terminal may be a microphone. Such a configuration makes it possible to transmit information by ultrasonic and sonic waves.

Further, to solve the above-described problems, a pairing method according to the present invention is a method for pairing a measuring device and an information terminal. The pairing method includes obtaining, by the measuring device, a predetermined measured quantity, displaying the measured quantity on the measuring device, transmitting, from the measuring device, measurement information including identification information identifying the measuring device, and the measured quantity, receiving the measurement information by the information terminal, displaying, on the information terminal, a value of the measured quantity included in the measurement information being received, receiving an input indicating whether or not a value of the measured quantity displayed on the measuring device and the value of the measured quantity displayed on the information terminal match each other, and when, in the receiving of the input, there is an input indicating that the value of the measured quantity displayed on the measuring device and the value of the measured quantity displayed on the information terminal match each other, or there is not an input indicating that the value of the measured quantity displayed on the measuring device and the value of the measured quantity displayed on the information terminal do not match each other within a predetermined time, storing, in the information terminal, the identification information of the measuring device that has transmitted the measurement information including the value of the measured quantity.

Further, the pairing method may further include, in a case in which the information terminal receives the measurement information transmitted from a plurality of the measuring devices, when, in the receiving of the input, there is not an input indicating that the value of the measured quantity displayed on the measuring device and the value of the measured quantity displayed on the information terminal match each other within a predetermined time, or there is an input indicating that the value of the measured quantity displayed on the measuring device and the value of the measured quantity displayed on the information terminal do not match each other, displaying, on the information terminal, a value of the measured quantity included in the measurement information different from the measurement information including the value of the measured quantity.

Advantageous Effects of Invention

According to the present invention, it is possible to reduce a work burden of a user when pairing a measuring device and an information terminal.

DESCRIPTION OF EMBODIMENTS

Specific embodiments of the present invention will be described below with reference to the drawings.

First Embodiment

Figure 4:
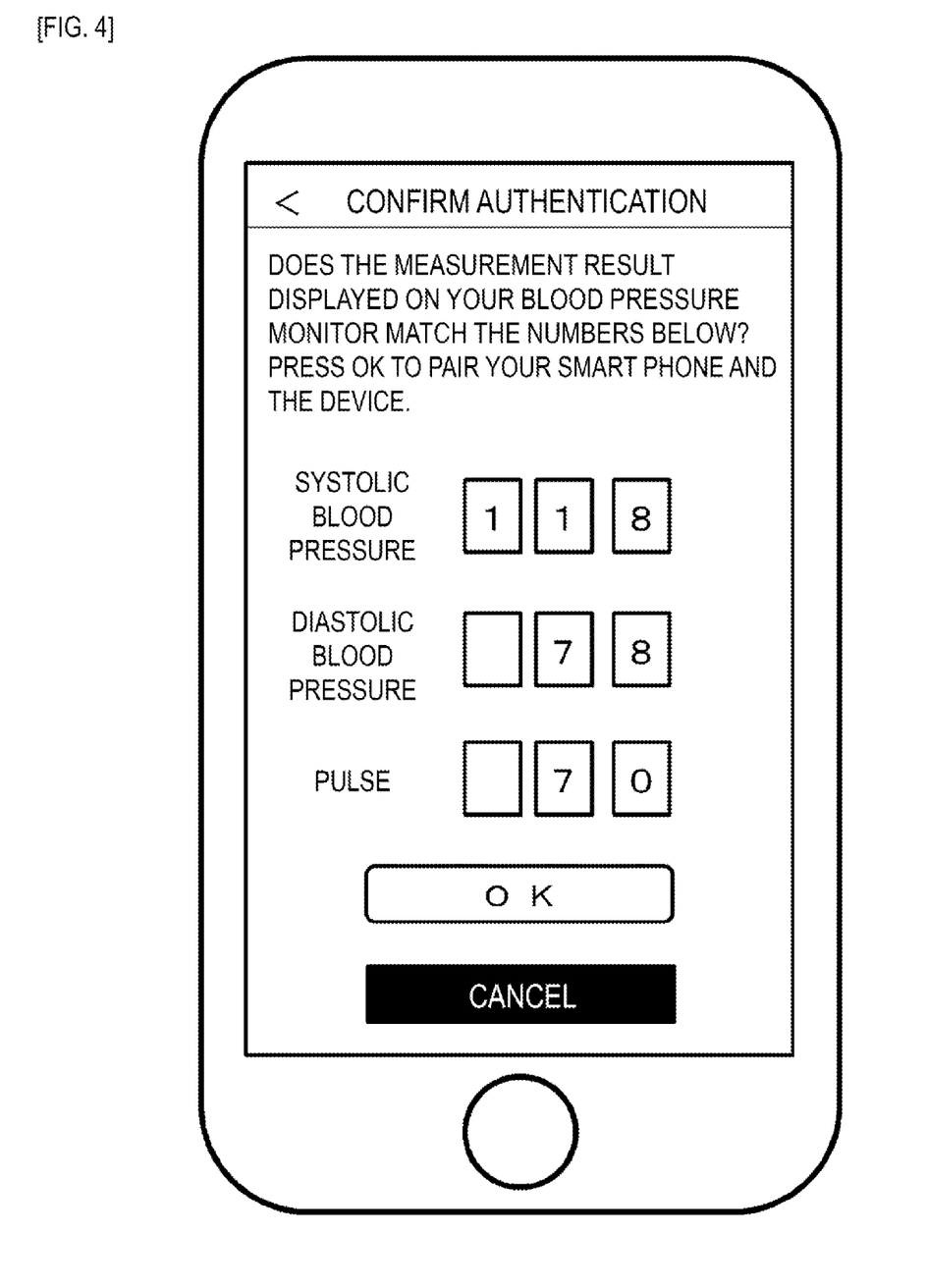
FIG. 4 is a diagram illustrating an example of a screen display of a smart phone of the information management system according to the first embodiment.

First, an example of the embodiments of the present invention will be described with reference to FIG. 1 to FIG.

4. However, the dimensions, materials, shapes, relative arrangements, and other characteristics of the components described in this embodiment are not intended to limit the scope of this invention unless otherwise indicated.

System Configuration

Figure 1:
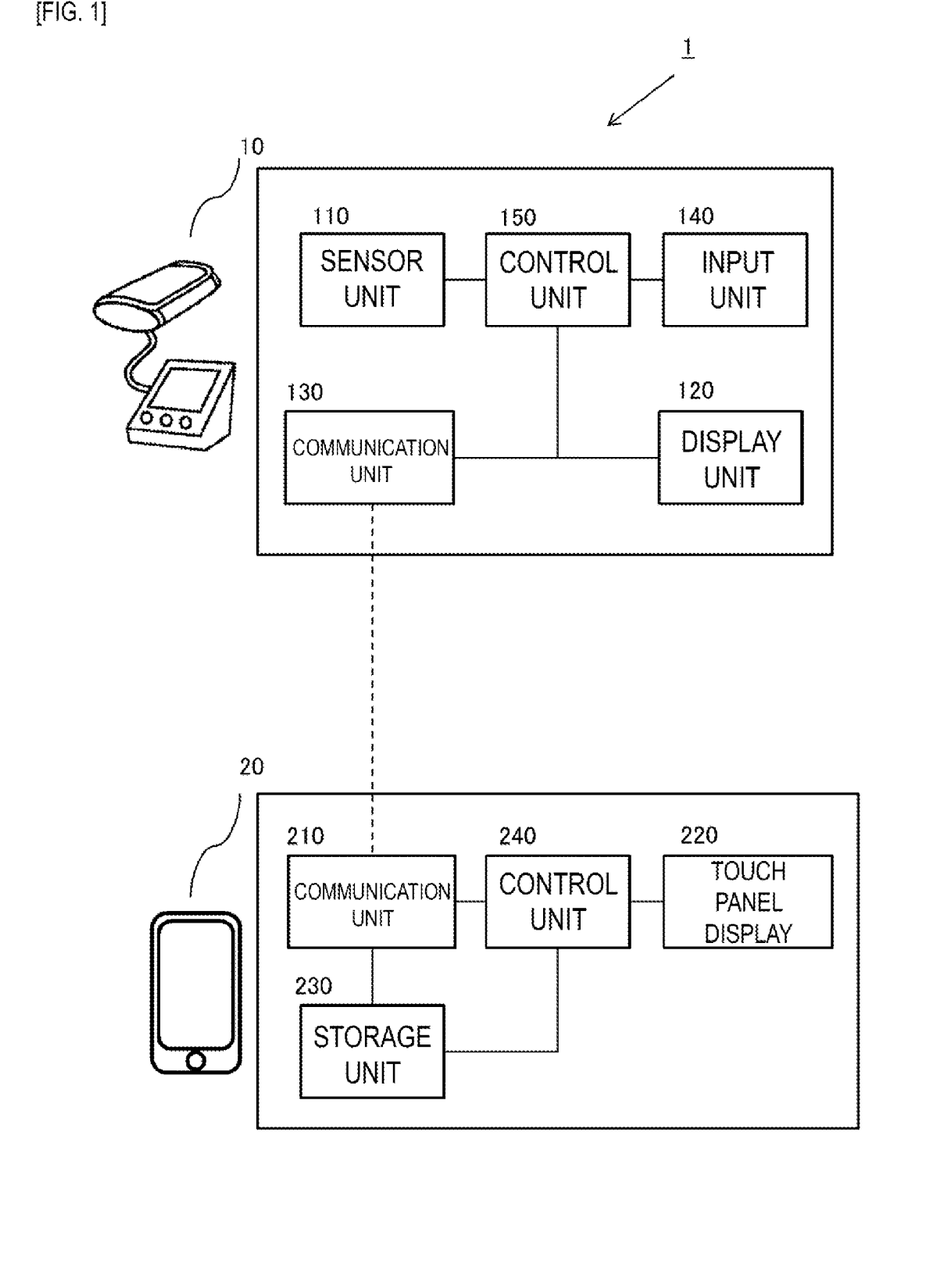
FIG. 1 is a block diagram illustrating an overview of a configuration example of an information management system according to a first embodiment.

FIG. 1 is a schematic diagram illustrating a configuration example of a health information management system 1 according to the present embodiment. As illustrated in FIG. 1, the health information management system 1 includes a blood pressure monitor 10 as an example of a measuring device, and a smart phone 20 as an example of an information terminal. The blood pressure monitor 10 and the smart phone 20 are configured to be capable of communicating by near-field wireless communication. The method of wireless communication is not particularly limited, and a method such as Bluetooth (trade name), infrared communication, and information transmission by ultrasonic waves can be employed.

Measuring Device

The blood pressure monitor 10 of the present embodiment is a measuring device that measures a blood pressure of a user using a so-called oscillometric method and, as illustrated in FIG. 1, is configured to include a sensor unit 110, a display unit 120, a communication unit 130, an input unit 140, and a control unit 150.

The sensor unit 110 includes a pressure sensor disposed in a cuff portion of the blood pressure monitor 10, and detects a pulse wave from a blood vessel of the user under an appropriate cuff pressure. The blood pressure monitor 10 of the present embodiment is capable of measuring a pulse in addition to a systolic blood pressure and a diastolic blood pressure on the basis of the pulse wave detected by the sensor unit. The values of the systolic blood pressure, the diastolic blood pressure, and the pulse are collectively referred to as blood pressure information. In the present embodiment, the blood pressure information corresponds to the measured quantity.

Figure 2:
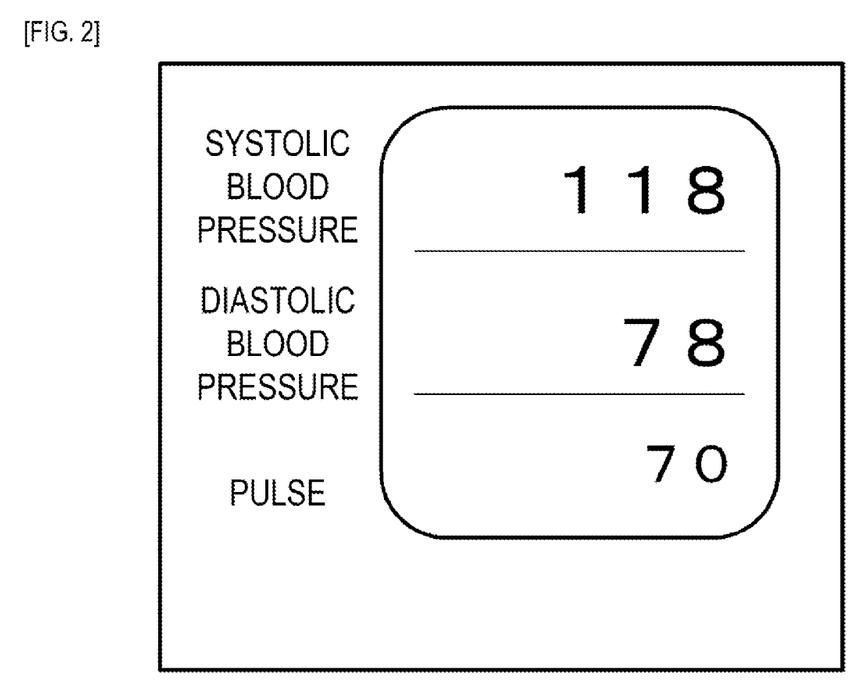
FIG. 2 is a diagram illustrating an example of a display screen of a blood pressure monitor of the information management system according to the first embodiment.

The display unit 120 is formed by, for example, a liquid crystal display, and displays the calculated blood pressure information. FIG. 2 illustrates an example of a display screen of the display unit 120. Note that, in the present embodiment, the display unit 120 corresponds to the first display unit.

The communication unit 130 is a communication unit capable of transmitting a signal used in near-field wireless communication, and a desired known technology can be adopted. Specifically, for example, the communication unit may be a communication antenna for bidirectional communication by radio waves such as Bluetooth (trade name), or a speaker that emits ultrasonic waves related to ultrasonic communication. That is, the communication unit 130 may perform transmission and reception (bidirectional communication) or may perform transmission only. The communication unit 130 transmits measurement information that includes identification information (for example, a serial number) unique to each blood pressure monitor, and the measured blood pressure information. Note that, in the present embodiment, the communication unit 130 corresponds to the first communication unit.

The input unit 140 is an input means such as a button or a touch panel display that receives input from the user, and receives various operations from the user, such as those for turning the power source on or off, starting measurement, and selecting an item.

The control unit 150 is a means for controlling the blood pressure monitor 10, and is configured to include a central processing unit (CPU), for example. Upon receiving an instruction from the user to start measurement via the input unit 140, the control unit 150 pressurizes the cuff and, under an appropriate cuff pressure, calculates the blood pressure information on the basis of the pulse wave detected by the sensor unit 110. Then, the calculated value is displayed on the display unit 120. In addition, each component of the blood pressure monitor 10 is controlled, and thus processing in accordance with the operation of the user via the input unit 140 is executed.

Information Terminal

As illustrated in FIG. 1, the smart phone 20, which is an example of the information terminal, is configured to include a communication unit 210, a touch panel display 220, a storage unit 230, and a control unit 240.

The communication unit 210 is a communication unit capable of receiving a signal related to near-field wireless communication, and a desired known technology can be adopted. Specifically, for example, the communication unit may be a communication antenna for bidirectional communication such as described above, or a microphone that receives ultrasonic waves related to ultrasonic communication. That is, the communication unit 210 may perform bidirectional communication or may perform reception only. The communication unit 210 is configured to receive the measurement information transmitted from the blood pressure monitor 10, and may be configured to communicate with other electronic devices or base stations as well. Note that, in the present embodiment, the communication unit 210 corresponds to the second communication unit.

The touch panel display 220 serves both as a display means and an input means, and displays the blood pressure information received by the communication unit 210. Further, operations from the user are received via various input images. Note that, in the present embodiment, the touch panel display 220 corresponds to the second display unit and the input unit.

The storage unit 230 is configured to include a main storage device such as a random access memory (RAM) and, for example, a long-term storage medium such as flash memory, and stores various types of information such as application programs and the measurement information.

The control unit 240 is a means for controlling a smart phone, and is configured to include, for example, a CPU, and executes various programs stored in the storage unit 230, thereby exhibiting the functions corresponding thereto.

Pairing Method for Measuring Device and Information Terminal

Figure 3:
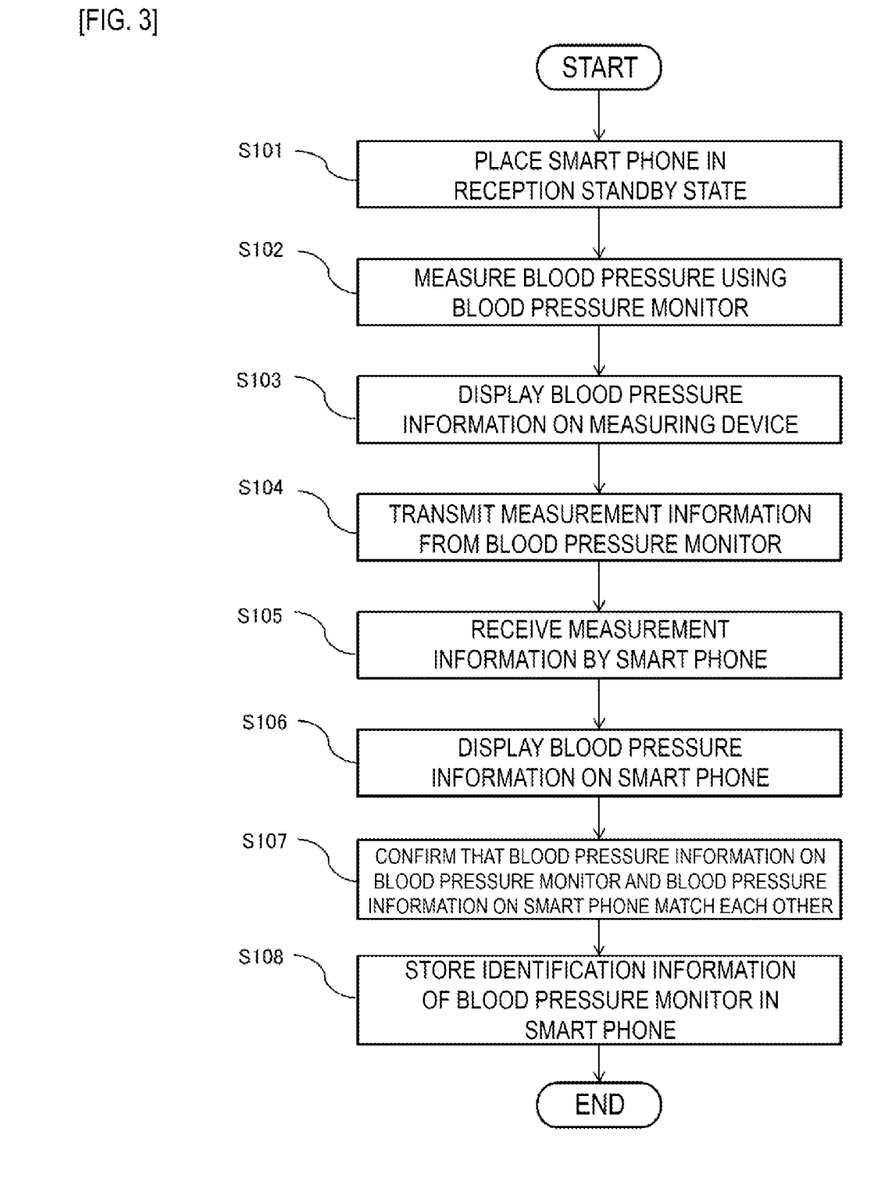
FIG. 3 is a flowchart illustrating processing of pairing in the information management system according to the first embodiment.

Next, a method for pairing the blood pressure monitor 10 and the smart phone 20 will be described. FIG. 3 is a flowchart illustrating a processing procedure when the blood pressure monitor 10 and the smart phone 20 are paired.

As illustrated in FIG. 3, the user first places, via the touch panel display 220 and the control unit 240 of the smart phone 20, the smart phone 20 in a standby state in which the measurement information can be received (step S101). Specifically, for example, an application program for health information management may be executed, and the control unit 240 may be configured to continually execute the application program in the background. Next, the user measures the blood pressure information by the blood pressure monitor 10 (step S102). Note that the blood pressure information in the present embodiment is information composed of three values: the systolic blood pressure, the diastolic blood pressure, and the pulse.

When the blood pressure information is measured in step S102, the control unit 150 displays the blood pressure information on the display unit 120 (step S103). Further, the control unit 150 generates measurement information including the blood pressure information and the identification information, and transmits the measurement information via the communication unit 130 (step S104).

Then, the measurement information transmitted in step S104 is received by the communication unit 210 of the smart phone 20 that waits to receive the information (step S105). Subsequently, the control unit 240 displays the blood pressure information included in the measurement information received in step S105 on the touch panel display 220 (step S106).

Furthermore, the control unit 240 requests the user to confirm that the blood pressure information displayed on the touch panel display 220 matches the blood pressure information displayed on the display unit 120 of the blood pressure monitor 10 (step S107). Specifically, it is sufficient to display, on the touch panel display 220, an operation button for carrying out an input indicating that the values match, or the like. FIG. 4 illustrates a display screen example for receiving the input of the user in step S107.

Upon receiving the input indicating that the blood pressure information displayed on the touch panel display 220 and the blood pressure information displayed on the display unit 120 match in step S107, the control unit 240 causes the storage unit 230 to store the identification information on the blood pressure monitor 10 included in the measurement information received in step S105 (step S108), and the series of processing ends.

With storage of the identification information in step S108, the specific blood pressure monitor 10 is identifiably registered in the smart phone 20, completing the pairing of the devices. After such pairing is performed, the control unit 240 displays, on the touch panel display 200, only the blood pressure information transmitted from the blood pressure monitor 10 that transmits the identification information stored in the storage unit 230 as the blood pressure information.

According to the configuration of a system such as described above, all the user has to do to pair the measuring device and the information terminal is to confirm that the value displayed on the display unit of the measuring device and the value displayed on the display unit of the information terminal match each other, and thus the user burden for pairing can be markedly reduced. Further, because it is not necessary to display the identification information on the measuring device or provide the information terminal with a configuration for reading the identification information, the cost for configuring the system can be reduced. Further, even in a case in which the information terminal receives the measurement information of a measuring device outside the system configuration, it is possible to prevent mistakenly pairing such a measuring device.

Modified Example

In the first embodiment described above, when there is an input indicating that the blood pressure information displayed on the touch panel display 220 matches the blood pressure information displayed on the display unit 120 in step S107, the processing proceeds to step S108. However, the processing does not need to be configured in this way. For example, in step S107, in a case in which there is not an input from the user within a predetermined time (for example, 10 seconds) indicating that the blood pressure information displayed on the display unit 120 and the blood pressure information displayed on the touch panel display 220 do not match, it may be assumed that an input indicating that the blood pressure information matches is received, and the processing may proceed to step S108.

Further, the step of displaying the measured blood pressure information on the display unit 120 of the blood pressure monitor 10 (step S103), and the step of generating and transmitting the measurement information (step S104) may be executed in the opposite order.

Second Embodiment

Next, another embodiment of the present invention will be described with reference to FIGS. 5 and 6. In the following, components that are the same as those in the first embodiment are given the same reference numerals, and detailed descriptions thereof will be omitted.

Figure 5:
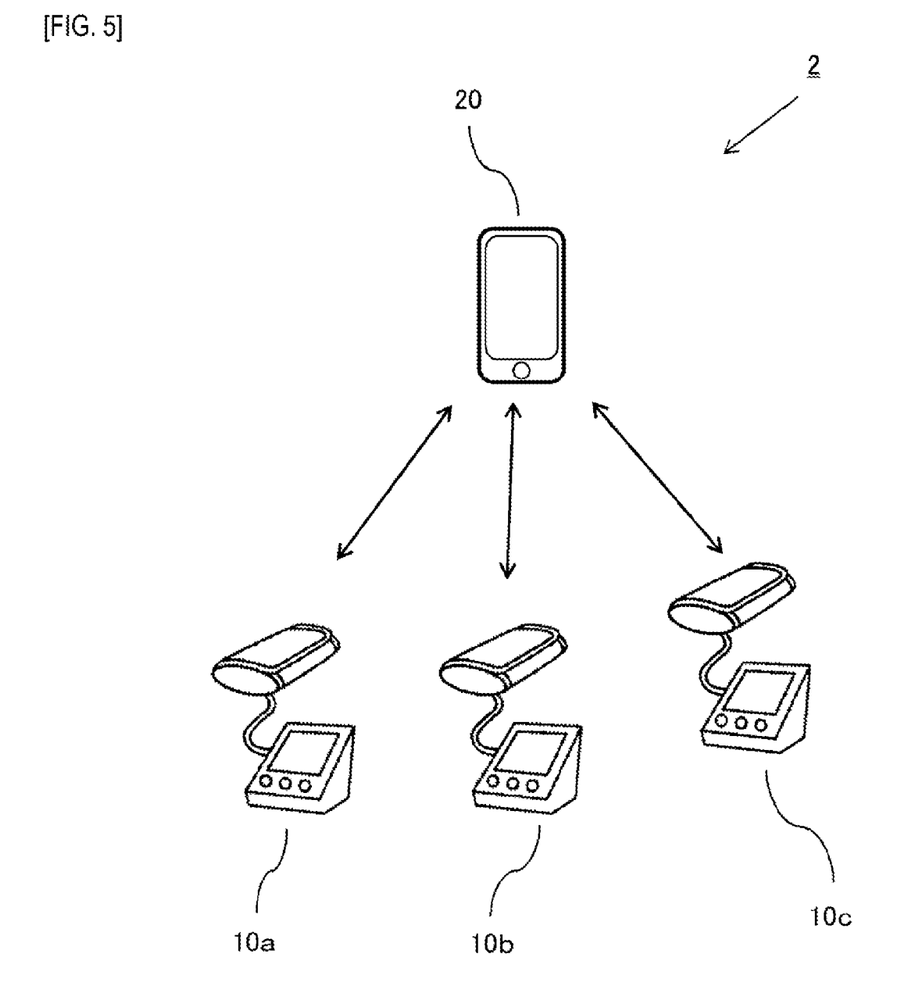
FIG. 5 is a diagram illustrating a configuration example of an information management system according to a second embodiment.

FIG. 5 is a schematic diagram illustrating a configuration example of a health information management system 2 according to the present embodiment. As illustrated in FIG. 5, the health information management system 2 includes a plurality of blood pressure monitors 10a, 10b, and 10c and the smart phone 20. The blood pressure monitors 10a, 10b, and 10c and the smart phone 20 are configured to be capable of communicating by near-field wireless communication. Note that the components of each of the blood pressure monitors 10a, 10b, and 10c, and the smart phone 20 are the same as those in the first embodiment, and therefore descriptions thereof will be omitted.

The health information management system 2 in the present embodiment, unlike the first embodiment, includes the plurality of blood pressure monitors, and thus the smart phone 20 may receive measurement information of a blood pressure monitor that is different from the blood pressure monitor used by the user for measurement. Therefore, in the processing when each of the blood pressure monitors 10 and the smart phone 20 are paired, a procedure different from that of the first embodiment is executed.

Figure 6:
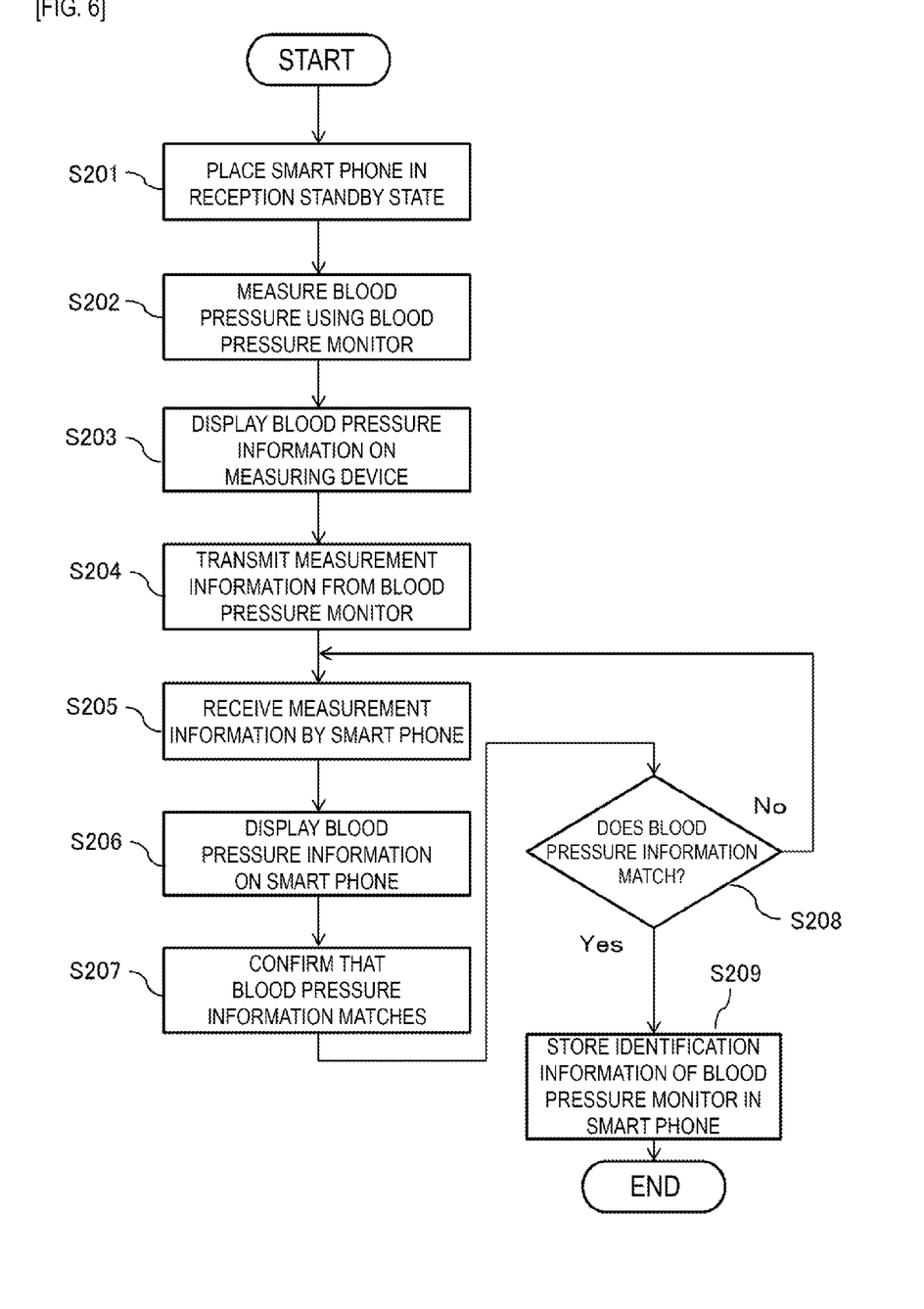
FIG. 6 is a flowchart illustrating processing of pairing in the information management system according to the second embodiment.

FIG. 6 is a flowchart illustrating a processing procedure when each of the blood pressure monitors 10 and the smart phone 20 are paired in the health information management system 2 of the present embodiment. The processing from step S201 to step S207 is similar to that of step S101 to step S106 of the first embodiment. That is, the user places the smart phone 20 in a standby state in step S201 and measures the blood pressure using the blood pressure monitor 10 in step S202. Then, the control unit 150 displays the blood pressure information on the blood pressure monitor 10 in step S203, and transmits the measurement information from the communication unit 130 in step S204. Furthermore, the control unit 240 receives the measurement information in the communication unit 210 in step S205, and displays the blood pressure information on the touch panel display 220 in step S206. Furthermore, the control unit 240, in step S207, requests the user to confirm that the blood pressure information displayed on the touch panel display 220 matches the blood pressure information displayed on the display unit 120. At this time, the confirmation screen displayed on the touch panel display 220 may be the same as that of the first embodiment, as illustrated in FIG. 4.

Next, the control unit 240 determines whether or not the blood pressure information displayed on the touch panel display 220 matches the blood pressure information displayed on the display unit 120 on the basis of the input from the user in step S207 (step S208). Here, in a case in which it is determined that the displayed blood pressure information matches, the processing proceeds to step S209 and the control unit 240 causes the storage unit 230 to store the identification information of the blood pressure monitor 10 included in the measurement information received in step S205, thereby completing the pairing and ending the series of processing.

On the other hand, in a case in which it is determined in step S208 that the displayed blood pressure information does not match, the measurement information of a blood pressure monitor that differs from the blood pressure monitor used by the user for measurement is considered to have been received, and therefore the processing returns to step S205, the measurement information from another blood pressure monitor is received, and the subsequent processing is repeated.

Note that, in a case in which the measurement information is received in step S205 after step S208, it is preferable to receive the measurement information excluding the measurement information that includes the blood pressure information for which a determination has already been made in step S208. For example, the measurement information that includes the blood pressure information for which a determination has already been made may be temporarily stored in the storage unit 230 as determined measurement information so that the measurement information thus stored is not received.

According to such a configuration of the present embodiment, even in a situation in which a plurality of measuring devices of the same type are used when pairing is performed, it is possible to pair the measuring device that the user has actually used for measurement and the information terminal.

Note that, in a case in which the communication system between the measuring device and the information terminal is bidirectional communication, that is, the measuring device can receive information from the information terminal, the measuring device can acquire information indicating that the pairing has been established with a specific information terminal. Therefore, displaying information indicating that pairing has been established on the display unit of the measuring device or the like makes it possible to easily confirm which measuring device of the plurality of measuring devices is paired with the information terminal. On the other hand, with unidirectional communication in which the measuring device only transmits information using ultrasonic waves or the like, information related to pairing establishment cannot be acquired in the measuring device. Therefore, when a plurality of measuring devices of the same type exist, normally it is not possible to easily confirm which measuring device is paired with the information terminal. In this regard, when the measuring device and the information terminal are paired using a system such as in the present embodiment, the user inevitably confirms which measuring device is being paired with the information terminal. As a result, the user can easily identify which measuring device is paired with the information terminal, and therefore the system according to the present embodiment is particularly suitable in a case in which the measuring device and the information terminal are paired by unidirectional communication.

Modified Example

Note that, in the second embodiment described above, the communication unit 210 may be configured to simultaneously receive the measurement information transmitted from the plurality of blood pressure monitors. In this case, in step S206, the blood pressure information of any one of the blood pressure monitors is alternatively selected as the blood pressure information displayed on the touch panel display 220. Here, in determining which blood pressure information is to be displayed, for example, the blood pressure information having high radio wave strengths at the time of reception of the measurement information may be prioritized. Further, in the case of the present modified example, when it is determined that the blood pressure information displayed does not match in step S208, the processing preferably returns to step S206 instead of step S205 to display the blood pressure information pertaining to another blood pressure monitor. Note that, at this time, the display preferably excludes the blood pressure information for which a determination has already been made in step S208. For example, the blood pressure information for which a determination has already been made may be temporarily stored in the storage unit 230 as determined blood pressure information so that the blood pressure information thus stored is not displayed.

Other

The description of each of the examples described above is merely illustrative of the present invention, and the present invention is not limited to the specific embodiments described above. Within the scope of the technical idea of the present invention, various modifications and combinations may be made.

For example, the measuring device may be a body information measuring device other than a blood pressure monitor, such as a scale, a body composition meter, a pulse meter, or a thermometer. Further, the measuring device may be an activity meter that measures the quantity of exercise in a pedometer, a tread mill, an Aerobike (trade name), or the like. In this case, the measured quantity displayed on the display unit may be the number of steps, a travel (walking) distance, or the like, may be a value such as the estimated number of calories consumed, or both. Additionally, the measuring device may be an environment sensor device that measures environmental information such as room temperature, humidity, noise, and illuminance.

Note that while, in the example described above, the system includes only one type of measuring device, the system may be configured to include a plurality of different measuring devices.

Further, the information terminal is not limited to a smart phone, and may be another mobile information terminal such as a tablet terminal, or may be a stationary terminal.

REFERENCE SIGNS LIST 1, 2 Environmental information management system
10 Blood pressure monitor
110 Sensor unit
120 Display unit
130, 210 Communication unit
140 Input unit
150, 240 Control unit
20 Smart phone
220 Touch panel display
230 Storage unit

The invention claimed is:
1. An information management system comprising:
one or more measuring devices; and
one or more information terminals,
each of the one or more measuring devices including
a sensor configured to measure a predetermined physical quantity,
a first display unit configured to display a measured quantity that is a value of the predetermined physical quantity measured by the sensor and/or a predeter- mined value calculated from the predetermined physical quantity measured by the sensor, and a first communication unit configured to transmit measurement information including identification information identifying the one or more measuring devices, and the measured quantity, each of the one or more information terminals including a second communication unit configured to receive the measurement information, a second display unit configured to display a value of the measured quantity included in the measurement information of one of the one or more measuring devices, the measurement information being received by the second communication unit, an input unit configured to receive an input indicating whether or not a value of the measured quantity displayed on the first display unit and the value of the measured quantity displayed on the second display unit match each other, a storage unit configured to store the identification information included in the measurement information received by the second communication unit, and a control unit configured to control the second communication unit, the second display unit, the input unit, and the storage unit, and when there is an input, via the input unit, indicating that the value of the measured quantity displayed on the first display unit and the value of the measured quantity displayed on the second display unit match each other, or there is not an input indicating that the value of the measured quantity displayed on the first display unit and the value of the measured quantity displayed on the second display unit do not match each other within a predetermined time, the control unit stores, in the storage unit, the identification information of the one or more measuring devices that has transmitted the measurement information including the value of the measured quantity.

2. The information management system according to claim 1, wherein in a case in which the second communication unit receives the measurement information transmitted from a plurality of the one or more measuring devices, when there is not an input indicating that the value of the measured quantity displayed on the first display unit and the value of the measured quantity displayed on the second display unit match each other within a predetermined time, or there is an input, via the input unit, indicating that the value of the measured quantity displayed on the first display unit and the value of the measured quantity displayed on the second display unit do not match each other, the control unit displays, on the second display unit, a value of the measured quantity included in the measurement information related to another of the plurality of the one or more measuring devices, the measurement information being received by the second communication unit.

3. The information management system according to claim 1, wherein the one or more measuring devices is any one of a scale, a body composition meter, a blood pressure monitor, a pulse meter, a thermometer, or a pedometer.

4. The information management system according to claim 1, wherein a communication unit of the one or more measuring devices is a speaker and a receiving unit of the one or more information terminals is a microphone.

5. The information management system according to claim 1, wherein the one or more information terminals is a smart phone.

6. A pairing method for pairing a measuring device and an information terminal, the pairing method comprising:

obtaining, by the measuring device, a predetermined measured quantity;

displaying the predetermined measured quantity on the measuring device;

transmitting, from the measuring device, measurement information including identification information identifying the measuring device, and the predetermined measured quantity;

receiving the measurement information by the information terminal;

displaying, on the information terminal, a value of the predetermined measured quantity included in the measurement information being received;

receiving an input indicating whether or not a value of the predetermined measured quantity displayed on the measuring device and the value of the predetermined measured quantity displayed on the information terminal match each other; and when, in the receiving of the input, there is an input indicating that the value of the predetermined measured quantity displayed on the measuring device and the value of the predetermined measured quantity displayed on the information terminal match each other, or there is not an input indicating that the value of the predetermined measured quantity displayed on the measuring device and the value of the predetermined measured quantity displayed on the information terminal do not match each other within a predetermined time, storing, in the information terminal, the identification information of the measuring device that has transmitted the measurement information including the value of the predetermined measured quantity.

7. The pairing method according to claim 6, further comprising:

a plurality of measuring devices including the measuring device, in a case in which the information terminal receives the measurement information transmitted from the plurality of the measuring devices, when, in the receiving of the input, there is not an input indicating that the value of the predetermined measured quantity displayed on the measuring device and the value of the predetermined measured quantity displayed on the information terminal match each other within a predetermined time, or there is an input indicating that the value of the predetermined measured quantity displayed on the measuring device and the value of the predetermined measured quantity displayed on the information terminal do not match each other, displaying, on the information terminal, a value of the predetermined measured quantity included in the measurement information different from the measurement information including the value of the predetermined measured quantity.

8. The pairing method according to claim 6, wherein the measuring device is any one of a scale, a body composition meter, a blood pressure monitor, a pulse meter, a thermometer, or a pedometer.

9. The pairing method according to claim 6, wherein the information terminal is a smart phone.

\* \* \* \* \*